(12) United States Patent
Shoenfeld

(10) Patent No.: US 6,439,500 B1
(45) Date of Patent: Aug. 27, 2002

(54) SCRUB RETURNS CABINET

(75) Inventor: Norman A. Shoenfeld, Livingston, NJ (US)

(73) Assignee: S&S X-ray Products, Inc., Brooklyn, NY (US)

( * ) Notice: Subject to any disclaimer, the term of this patent is extended or adjusted under 35 U.S.C. 154(b) by 0 days.

(21) Appl. No.: 09/495,685

(22) Filed: Feb. 1, 2000

(51) Int. Cl.⁷ .............................. B65H 39/14; B30B 9/00
(52) U.S. Cl. ........................................ 242/528; 100/49
(58) Field of Search ........................ 242/528; 221/281, 221/253; 100/49, 102, 137, 144, 193, 151, 152, 221

(56) References Cited

U.S. PATENT DOCUMENTS

| | | | |
|---|---|---|---|
| 2,981,492 A | * 4/1961 | Simjian | 242/528 |
| 3,696,737 A | * 10/1972 | Wikner | 100/49 |
| 3,728,849 A | * 4/1973 | Lundahl | 100/226 |
| 5,713,270 A | 2/1998 | Fitzgerald et al. | 100/49 |
| 5,829,349 A | 11/1998 | Fitzgerald et al. | 100/102 |
| 6,223,934 B1 | * 5/2001 | Shoenfeld | 221/287 |

* cited by examiner

*Primary Examiner*—William A. Rivera
(74) *Attorney, Agent, or Firm*—Bernhard P. Molldrem, Jr.

(57) ABSTRACT

A scrubs returns cabinet for hospital workers to return surgical garment tops and bottoms. A cabinet housing has a door, drawer or similar port through which the customer places the soiled scrub suit after entering customer identification information. There are first and second belts in the housing that unwind from respective back and front reels or drums, and wind over a series of rollers or idlers onto a lower collecting drum. The scrubs fall onto one of the belts, and then are captured between the belts. The scrubs are compressed onto the collecting drum. The direction of travel of the belts is reversed to expel the soiled scrubs from the cabinet. These can be discharged directly into a laundry bin, so that the laundry attendant does not have to reach into the cabinet to retrieve the scrubs. The cabinet can be configured for the return of towels or other articles, or for dispensing such articles.

12 Claims, 3 Drawing Sheets

SCRUB RETURNS CABINET

BACKGROUND OF THE INVENTION

This invention relates to devices and techniques for vending or dispensing and receiving articles, and is especially directed to a returns cabinet in which hospital garments, i.e., scrubs can be received and held until they can be taken to a laundry facility. The invention is more specifically concerned with a belt-type returns unit, in which hospital scrub tops and bottoms are accepted and stored in a system of belts or webs, and which can be unloaded for laundering by reversing the direction of the belts.

Surgical scrubs are a type of hospital or surgical garment, most typically, the green shirts and pants that are worn in hospital operating rooms. These garments are issued to hospital personnel and serve to prevent contamination between patients and health workers. When the hospital personnel doff the garments, or when the scrubs become soiled or contaminated, they are expected to return them. Often this involves simply tossing the garments into a laundry basket, or else onto the floor, and with no control over who has or has not returned their scrub suits. Recently, there has been an effort to use a scrub return facility to account for these garments. Dispensers and return units may be tied to a network in the hospital laundry facility to keep track of the numbers and sizes of scrub tops and bottoms checked out to each of the hospital personnel, and to alert laundry personnel when a dispenser is running out of garments, if the returns unit is full, or if a machine becomes jammed or inoperative for some reason.

Hospitals and clinics usually provide scrubs to surgeons, nurses and attendants at no cost to them. For purposes of this discussion, the surgeons, physicians, nurses, visitors, and others who obtain scrubs can be considered "customers." Each customer is permitted to have some limited number of scrubs outstanding at any one time, and is expected to return the scrubs to the return facility when they have been worn or if they become soiled. Traditionally, hospitals would leave a stack of clean scrubs in the changing rooms for the physicians, nurses and staff. These would have a tendency to disappear during the day, and would not be available later in the day or in the evening. This led physicians to hoard scrubs in their locker so they would not be caught without scrubs in the evening. This hoarding has led to shortages, which led to greater hoarding. Another method was to assign a hospital attendant with the task of issuing scrubs to customers, but with no real control or accounting for how many scrubs were dispensed. Soiled scrubs were returned by leaving them in laundry carts in the changing rooms, or simply leaving them lying on the floor of the changing room. However, even with this limited level of control, because the hospital must be open at all times, and because fresh scrubs may be needed in any and all the various surgery facilities within the hospital, staffing the laundry attendant position has become a burden on the hospital. For these reasons, there has been much interest recently in automating the issuance and return of hospital garments. In addition, there remains the need to account for the numbers of scrub tops and bottoms issued to each customer, as well as the need to maintain data concerning scrub usage for purposes of re-stocking.

One example of a vending or dispensing device for hospital garments of this type is described in Fitzgerald et al. U.S. Pat. No. 5,638,985, and an associated scrubs return cabinet is described in U.S. Pats. Nos. 5,713,270 and 5,829,349. This return cabinet can be connected to a computer server in the laundry for accounting for the scrubs and crediting the customers for returned scrubs. Here, access to the unit is obtained by inputting customer identification, either on a bar code reader or a keypad. This then permits the bin door to be opened, and credits the customer for the return of the scrub suit. There is a video camera and video cassette recorder or VCR in the unit which videotapes images of the scrubs as they are being returned, and may also videotape an image of the customer's face. In order to compact the garments that fall into the bin, the scrubs return cabinet has an arm assembly that swings down to compress the returned scrubs. To remove the scrubs from the unit, the laundry attendant has to open the doors on the front of the unit and reach down into the bin to retrieve the soiled scrubs.

It was desired to create a scrubs return cabinet with additional advantages, such as receiving the scrubs at a convenient level so that the customer does not have to bend down, and which can accurately credit the customer for the garments returned. It was also desired to make it possible for the laundry attendant to retrieve the returned scrubs in an automated or mechanized fashion by discharging them into a laundry bin.

It is also desired to create a returns system and technique that can be used with articles other than hospital garments, such as towels which may be issued to guests at a hotel swim pool or fitness facility.

OBJECTS AND SUMMARY OF THE INVENTION

Accordingly, it is an object of the present invention to provide a garment returns cabinet or station that avoids the drawbacks of the prior art.

It is another object to provide a returns cabinet that facilitates customers' return of soiled hospital scrubs and which facilitates retrieval of the scrubs for laundering.

An improved scrubs dispensing or vending facility is the subject of a separate patent application by the same inventor.

In accordance with an aspect of the present invention, a returns cabinet receives hospital garments to be picked up and laundered, and credits the customer with the return. In a rather compact cabinet housing there is a return port or loading door for the customer to place the hospital garment (s) to be returned. The customer inputs a keypad and/or a badge or card reader to allow the loading door to be opened. This enters the customer's ID, as well as an identification of the scrubs being returned. Within the cabinet housing is a system of belts and reels that capture the scrubs and compress them until they can be discharged to the laundry attendant. A back reel within the cabinet housing supplies a first web belt that is wound on it and a front reel housing supplies a second web belt that is wound it. A lower reel or drum, i.e., a take-up reel in the cabinet housing takes up both said first and second web belts together, as well as any returned scrubs that are captured between the belts. Drive motors with or without clutches turn these reels. A system of idlers and rollers defines a path for the belts from their respective front and back reels to the lower reel. This belt path is configured such that a portion of one of the first and second belts defines a landing spot or zone where the returned garment falls after it is placed in the return or load port, which can be a drawer or door. The cabinet may contain a controller board that is coupled to customer input (keypad or badge reader) and to the motor drive. This controls the rotation of the reels such that garments received on said landing spot travel on the belt(s) toward the take-up reel. The soiled scrubs are captured between the first and second belts, and compressed between the belts onto the lower reel. The compression of the soiled scrubs between the two belts on the lower drum is extremely effective in increasing the storage capacity of the return unit.

A digital camera within the upper part of the cabinet housing records images of garments placed into the cabinet before they are wound onto the belts. The digital camera can also record the associated customer ID information, either from an LED display or recorded electronically. The digital images can be recorded on a computer-type magnetic disk drive, either within the cabinet or in the laundry facility. If foreign material (i.e., items other than scrubs) is found in the unit, the digital pictures can be quickly and easily retrieved by the laundry personnel, and the user or customer identification for this foreign matter can be found. If, as should normally be the case, only scrubs are found in the unit, then the stored images can be erased from the magnetic disk without need for review.

An advantage of this system is the ease with which the soiled garments can be retrieved from it. A discharge door is located on the front of the cabinet housing, and is opened by laundry personnel to permit discharge of returned scrubs from the cabinet. A laundry bin can be placed below this door, and the controller board actuated so that the reels turn in a reverse direction. The belts unwind from the lower or take-up reel, and bring the scrubs forward that are compressed on the reel. The scrubs are discharged through the discharge door and into the bin. This occurs without the attendant having to reach into the machine. Also, the returned scrubs are stored on the belts in the order in which they are returned, and are discharged in the reverse order. If there are any foreign articles discharged from the cabinet, they will also be discharged in the same order. This makes it simple for the laundry attendant to estimate when the foreign articles were returned, and facilitate finding the recorded images and ID information on the magnetic disk.

In one embodiment, the return port or load door may be in the form of a drawer that is positioned at or near the cabinet, i.e., above the landing spot of the belt(s). The drawer can be pulled out from the cabinet housing to an open position, and the returned scrubs can be laid in the open drawer. Then, when pushed in to a closed position, the drawer rocks down and permits the garment to drop to the landing spot. The drawer may have a divider so that a scrub tops are placed to one side of the divider and scrub bottoms placed to the other side of the divider.

Alternatively, the return port may be a top-loading door at a top of the cabinet housing.

Preferably the scrub tops and scrub bottoms are wound up on the left and right sides of the belts, or else on different belt systems, in order to make even the distribution of scrubs being stored. The load door or drawer may also have a sensor to ensure that the tops and pants or bottoms are loaded on the correct sides of the drawer. The scrubs are wound tightly on the lower reel or drum, which compresses them to achieve maximum storage. The scrubs are tracked to fall and be captured between the two belts, and then wound onto the lower belt. The belts are advanced for each scrub or set of scrubs returned. The belts may be of a plastic resin material, such as polyethylene, polypropylene, vinyl, reinforced vinyl, sheet material made of HDPE fibers (sold by Dupont as TYVEK), or another suitable material. The belts may favorably be of an open mesh material, and may be either a disposable material or a washable material. The drive mechanisms for the reels or drums can be chain drive or belt drive.

A cabinet made according to these same basic principles can be configured as a dispensing unit, e.g., as a towel dispenser for hotel poolside use. In that case, the towels could be pre-loaded and dispensed to hotel guests one at a time, by running the belts in the direction from the lower drum toward the other reels or drums.

The laundry computer system may also track the order in which given sizes of scrub suits are returned during the day, either for statistical or other purposes.

As aforesaid, the associated scrubs dispensing mechanism and technique are the subjects of a separate invention, and that is disclosed in U.S. Pat. Appln. Ser. No. 09/483,961 now U.S. Pat. No. 6,223,934.

The above and many other objects, features, and advantages of this invention will become apparent from the ensuing description of a selected preferred embodiment, which is to be considered in connection with the accompanying Drawing.

DETAILED DESCRIPTION OF THE PREFERRED EMBODIMENT

Figure 2:
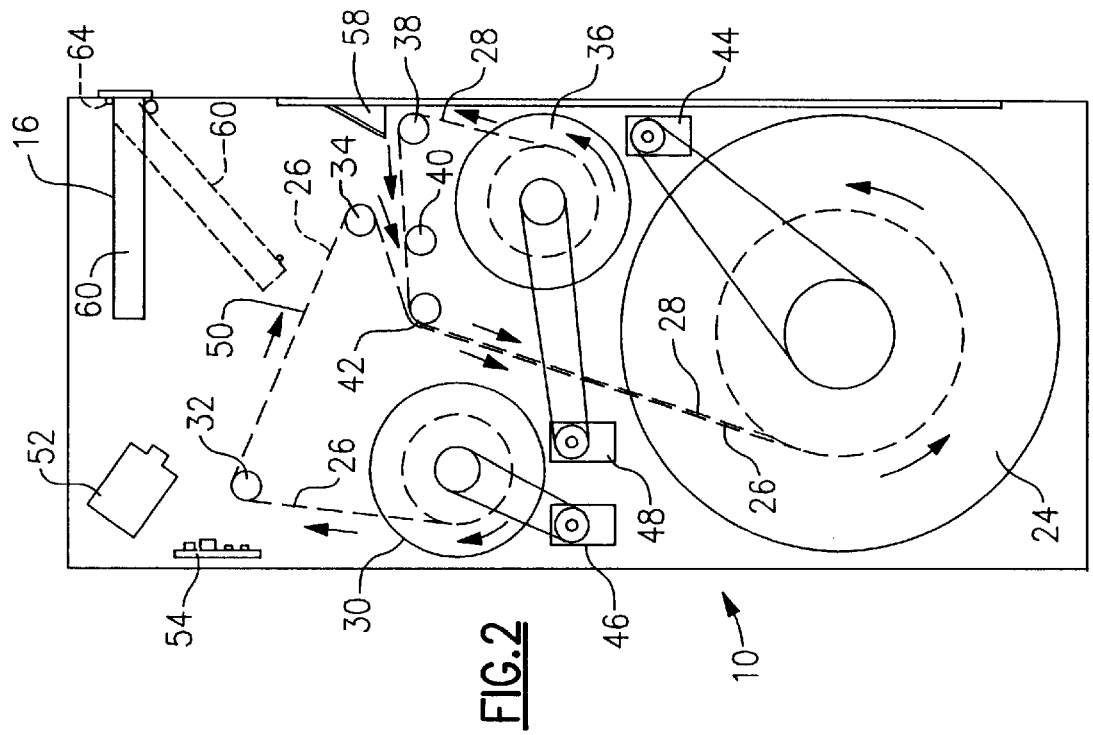
FIG. 2 is a schematic side elevation of this embodiment.
Figure 1:
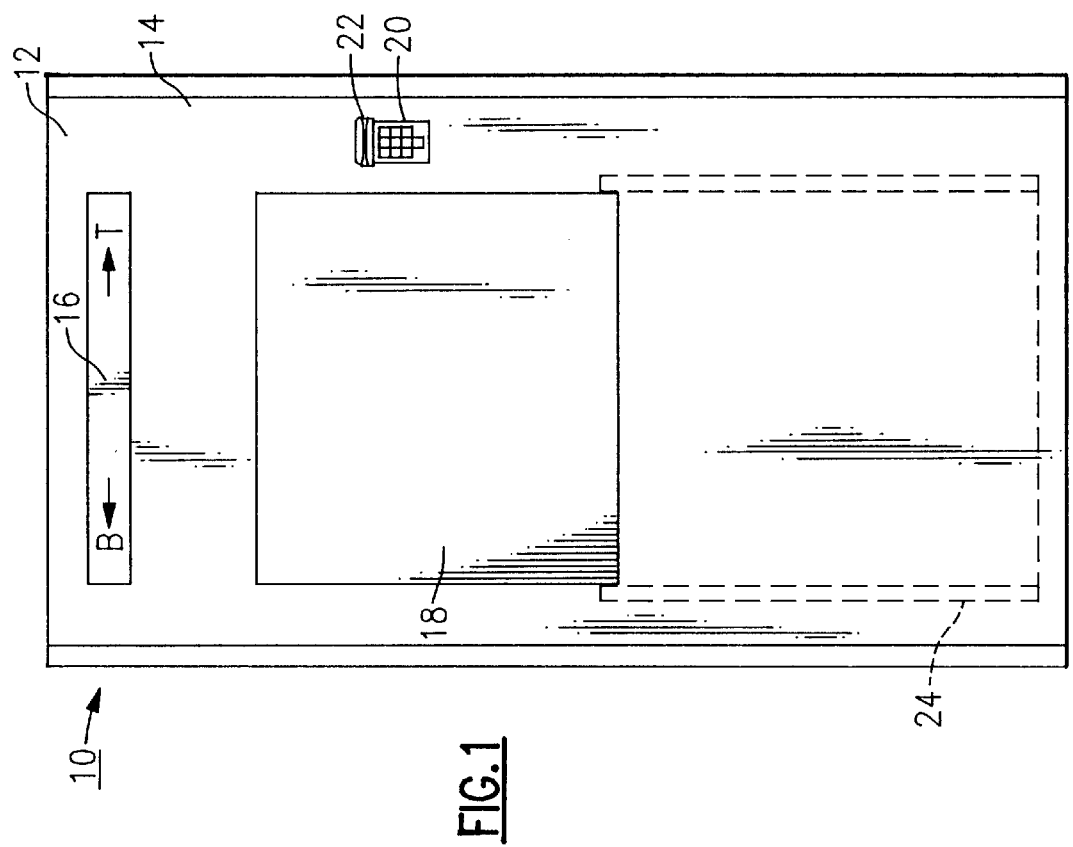
FIG. 1 is a front elevational view of a hospital scrubs returns cabinet, according to one preferred embodiment of the invention.

With reference to the Drawing, and initially to FIGS. 1 and 2, a hospital scrubs returns cabinet 10 is configured to permit a customer, i.e., a nurse, doctor, or other hospital employee, to return scrub tops and scrub bottoms when they have become soiled or contaminated, or when the customer has changed out of them after completing a shift or surgical procedure. The return cabinet has a main enclosure 12 formed of a top, back, bottom and side walls, and a front panel 14. At the top center of the panel is a load port or drawer 16 where the customer can insert the garments to be returned. In this embodiment, the drawer pulls out for loading, and when the customer has loaded it with his or her return scrubs, the drawer is pushed shut to permit the mechanism inside the cabinet to collect and store the scrubs. This drawer 16 may be manually opened and closed, or may have a motorized mechanism. Beneath this drawer 16 is a discharge door 18, which may be opened by laundry personnel for discharge of the stored returned scrubs, i.e., into a laundry bin or basket (this is discussed later). A keypad 20 permits customer entry of customer identity, PINs or access codes, and identification of the type and number of scrubs to be returned. There may also be a display feature here, which is not shown in this detail. Above the keypad 20 may be a card reader or badge reader, here a card-swipe mechanism 22 for reading either a bar code on the customer badge or ID card, or reading a magnetic stripe on the card or badge. Other customer identification mechanisms are available and could be used, such as an interrogator that sends an interrogation signal for a short distance in front of the cabinet, and then waits for an electronic response from the customer card or badge.

Figure 3:
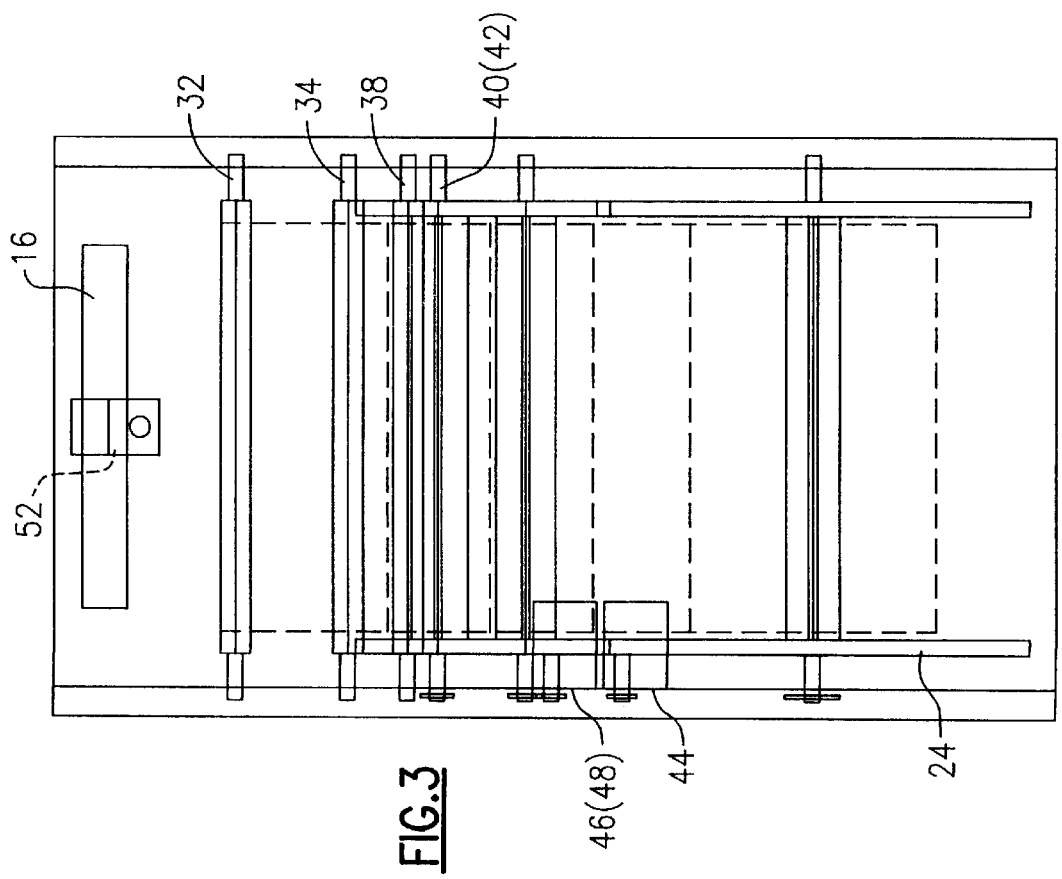
FIG. 3 is a schematic front elevation of this embodiment, showing its interior workings.

As also shown in FIGS. 2 and 3, within the cabinet housing 12 there is a lower collecting drum or reel 24, onto which are wound a first conveyor belt 26 and a second conveyor belt 28. The first belt 26 is supplied from a rear supply drum or reel 30, from whence it travels on a path over a first idler or roller 32 and a second idler or roller 34. The second belt 28 is supplied from a front supply drum or reel 36, and this belt 28 travels on a path over a series of idlers or rollers 38, 40, and 42, in the direction of travel from the supply reels 30, 36 toward the collecting reel 24. The two belts 28, 30 converge at the roller 42, so that they capture any articles place on them, and wrap the articles onto the collecting reel 24. The belts 26, 28 may be a closed or open web, e.g., an open mesh, and may be of plastic, i.e., polypropylene, vinyl, TYVEK, or other suitable material. The belts may be made of a disposable material, i.e., fiber-based or other material which is inexpensive and may be discarded or burned without significant environmental impact.

There is a belt or chain drive mechanism 44 associated with the lower collecting reel 24, which may include a motor and clutch drive. There are also similar drive mechanisms 46 and 48 for the rear and front reels 30 and 36, respectively. As illustrated in FIG. 2, a landing zone or area 50 is defined on one or the other of the belts 26, 28, where the scrubs placed into the drawer 16 are dumped when the drawer 16 is placed into its closed position. As shown here, the drawer 16 has a pivoting tray, which when open permits the customer to lay the scrub top and bottom into the drawer 16, but when closed pivots down (shown in broken lines) to drop the scrubs onto the belt 26 (or 28). Then, the drawer tray 60 returns to the upper (solid line) position to receive return scrubs from the next customer.

In this embodiment, the cabinet has an overall height, width (left to right), and depth (front to back) that provides a relatively small footprint so that the cabinet 10 occupies a minimum of hospital floor space. The load door or drawer 16 is situated at a height of about 36 inches to 48 inches above the floor, which is a convenient height for doctors, nurses, attendants, or other customers. The base of the unload door 18 may be about 18 to 24 inches above floor level, to facilitate discharge of the soiled scrubs into a laundry bin or hamper.

Within the cabinet 12, a digital camera 52 is positioned to capture images of the scrubs or other articles on the tray 60 as they drop to the belt 26. There is also an associated microprocessor-based controller board 54 with the necessary modules to connect with and control the keypad 20, card or badge reader 22, motor drives 44, 46, 48 and camera 52. The board 54 may also have network modules, e.g., Ethernet circuitry, to connect the return cabinet with the hospital laundry computer network, either directly or via a modem. The controller board 54 may favorably have an associated magnetic memory, i.e., disk drive, for storing digital images from the camera 52. Digital camera images are preferably stored on the network computer in the laundry (or alternatively, in a memory in the returns unit itself, which may be useful if the network is not functioning). Images are stored of the articles returned into the return cabinet, together with images of the customer identification. The latter can be entered either visually, i.e., from an LED display, or else electronically. The board 54 may be coupled via a wiring harness or other connection to the input devices, such as the keypad 20 and badge reader 22, and may also be network-connected to a main hospital computer or to a laundry facility system computer.

Figure 4:
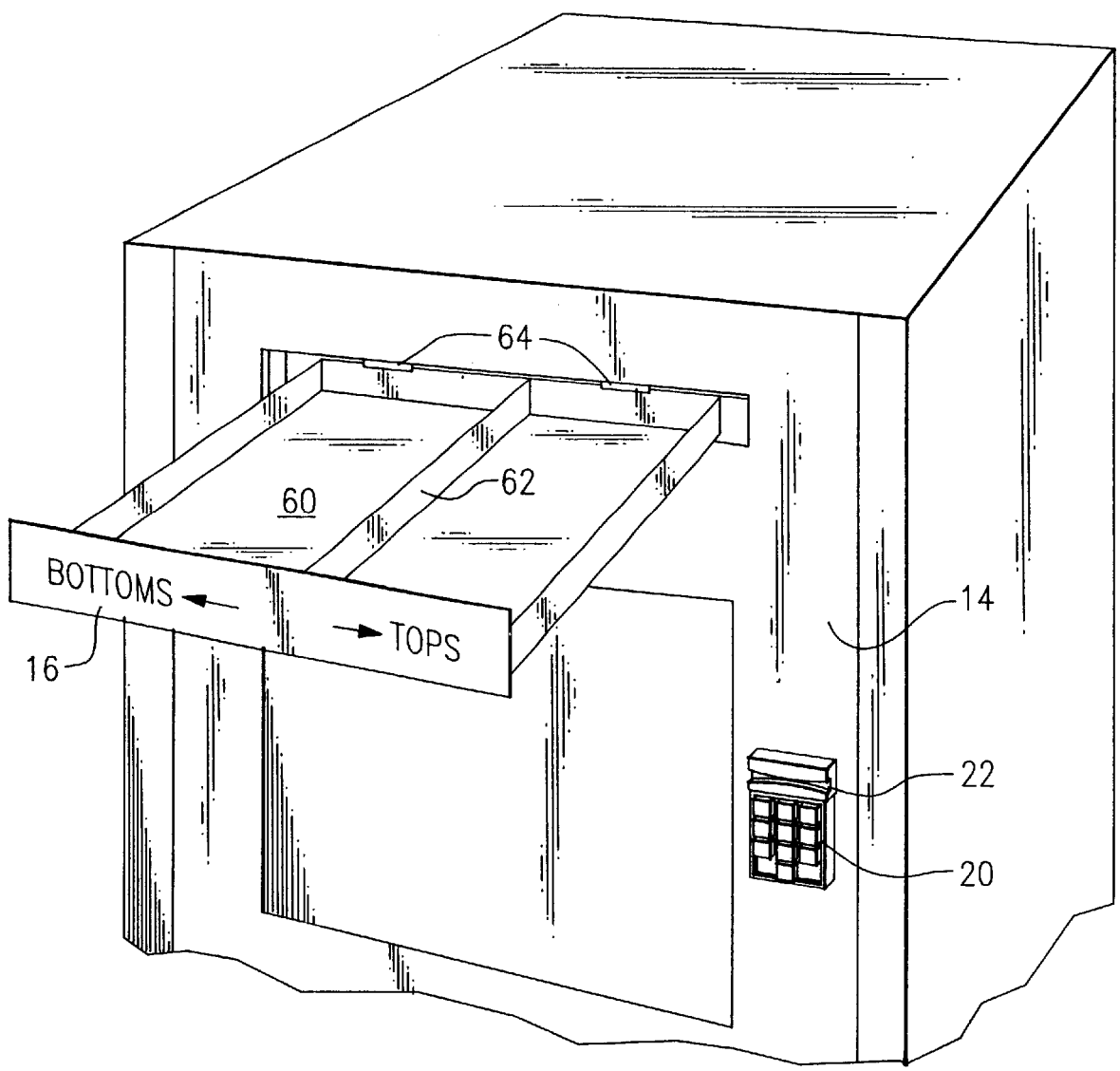
FIG. 4 is perspective view showing the returns drawer of this embodiment

As shown in FIG. 4, the drawer 16 has a bottom or tray portion 60 with a divider 62 that divides the tray 60 into left and right portions. Customers are directed to place the tops on one side of the divider, and to place the bottoms or trousers on the other side. This arrangement lets the belts 26, 28 and the lower reel 24 fill more evenly. There may be sensors 64 to detect presence of the scrubs in either portion of the tray 60.

A customer approaching the machine with a soiled scrub suit enters his or her customer information into the keypad 20 (or by using the card reader 22, or both). Then, the drawer 16 opens forward, permitting the customer to lay the top and bottom scrubs into it. When the drawer closes, the scrubs drop down onto the landing zone 50 of the belt 26, and the drive 44 is actuated to advance the belts 26, 28. The scrub suits are captured between the belts 26, 28. Each time a scrub set is loaded into the cabinet the belts are advanced onto the lower reel 24. In this way, the scrub suits are loaded onto the lower reel 24 and are compressed between the two belts. The use of a load drawer with separate compartments for tops and bottoms keeps the garments better distributed on the conveyor belts 26, 28 for more uniform compression. There may be a guide 58 at the front door 18 for directing scrubs onto the belt 28. Compressing the soiled scrubs between the belts 26 and 28 increases the capacity of the return unit, as compared with a standard scrubs return bin of the same general size.

When the laundry attendant comes to remove the soiled scrubs from the cabinet, he or she opens the door 18 and keys the machine, e.g., by entering a code on the keypad. The front door 18 can swing up or drop down, depending on the design. This also actuates the drives 46 and 48 to run the belts in the opposite direction from that used for loading. That is, the belts 26, 28 unwind from the lower reel 24 and wind onto the rear and front reels 30 and 36. The conveyor direction is reversed, and the scrub suits are propelled out through the front of the unit, so that they fall into a laundry bin or hamper placed at the front of the unit. The laundry attendant does not have to reach down into the bottom part of the cabinet to retrieve the soiled scrubs.

The digital camera 52 records what was returned, with a view of the tops and pants compartments and a view of the associated customer ID. The digital pictures are temporarily stored in magnetic memory, either in the cabinet or in a server in the laundry, and can be erased after the garments are inspected and washed in the laundry. If objects other than scrubs were returned, then the stored images can be quickly retrieved and reviewed to identify which customer deposited these foreign articles. If this occurs, the laundry can send a notice to the customer and take appropriate action.

The return unit is favorably networked to the laundry network to credit the customer(s) with the return of their scrubs. The hospital laundry system may also keep track of the current capacity of the various return cabinets stationed around the hospital or clinic, and can flag an operator whenever one of the return cabinet becomes full and needs emptying. The system may also flag maintenance personnel if a machine jam is detected. The device of this same invention can easily be adapted to control the return of towels in hotels or health clubs. In that case, the guests or members may use their hotel key card or member to obtain credit for the return (against a room account or a member account).

A dispensing arrangement can be constructed according to these same principles, in which articles are stored on a lower reel, and are dispensed one at a time by rewinding a pair of belts onto a pair of upper rollers.

Figure 5:
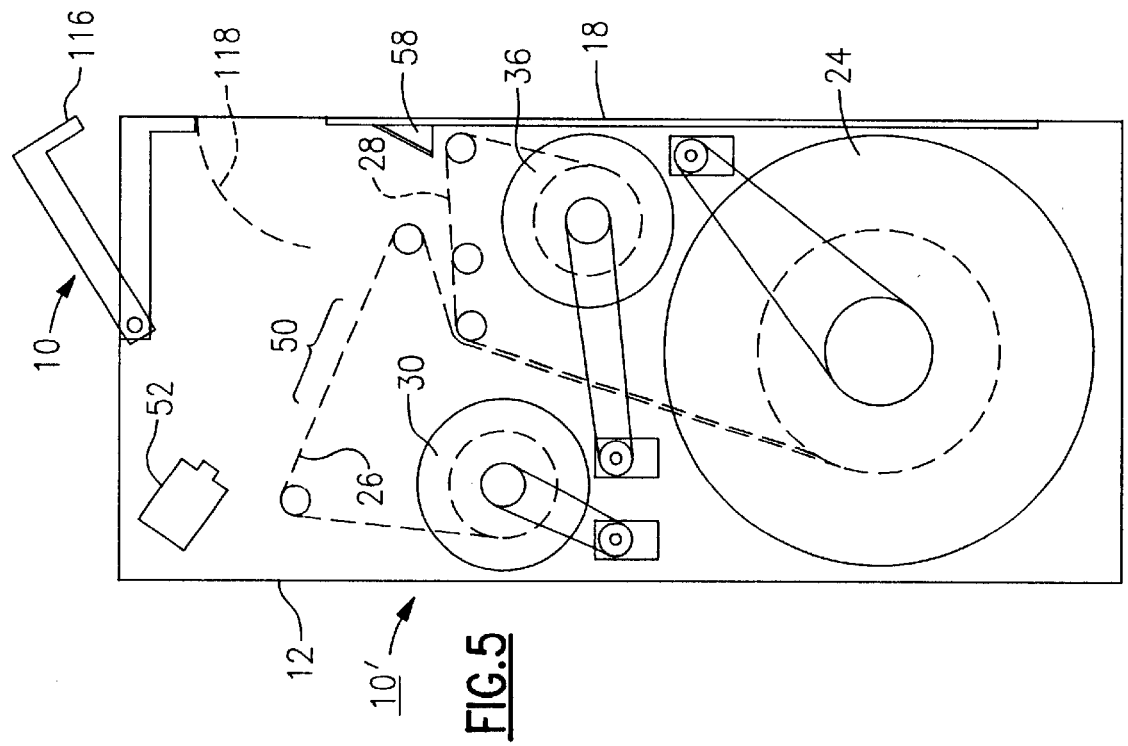
FIG. 5 is a schematic side elevation of another embodiment.

An alternative arrangement is shown in FIG. 5, in which similar elements to those described in reference to the first embodiment are identified with the same reference numbers, and for which the description will not be repeated. Here, there is a top loading door 116 through which the customer returns soiled scrubs. A guide or track 118, shown in ghost lines, guides the scrubs to the landing zone 50 on the belt 26. Otherwise, this cabinet is identical to the first embodiment.

While the invention has been described in terms of a hospital scrub return or receptacle arrangement, a unit incorporating the principles of this invention could be used for other returnable items. Similar machines may be used to receive non-surgical garments, such clean-room cloaks or lab coats, or for towels in a hotel or health-club environment. In the latter case, the hotel or club guest could access the machine with a membership card or room key card. The machine is ideal for holding such soft foldable items, which may be compressed on the belt when wound onto the reels. However, the receiving cabinet could be used for receiving returns generally, or vending or dispensing other items, generally.

While the invention has been described hereinabove with reference to a preferred embodiment, it should be recognized that the invention is not limited to that precise embodiment. Rather, many modification and variations would present themselves to persons skilled in the art without departing from the scope and spirit of this invention, as defined in the appended claims.

I claim:

1. Returns cabinet which is adapted for a customer to return hospital garments to be picked up and laundered, comprising a cabinet housing; a return port in said cabinet housing for the customer to place a hospital garment to be returned; customer input means adapted for said customer to input identification information and to initiate a return procedure; a first supply reel within said cabinet housing supplying a first web belt that is wound thereon; a second supply reel within said cabinet housing supplying a second web belt that is wound thereon; a collecting reel in said cabinet housing taking up both said first and second web belts; drive means for turning said reels; means defining a path for said first and second web belts between the respective supply reels and said collecting reel; such that a portion of one of said first and second belts defines a landing zone where said one belt receives the garment placed in said return port; and controller means coupled to said customer input means and said drive means for controllably turning the reels such that garments received on said landing zone travel on said one belt along said path towards said lower reel, and are captured between said first and second belts and are compressed between said belts on said collecting reel.

2. A scrubs return cabinet according to claim 1, further comprising a camera within the cabinet housing for recording images of garments placed into the cabinet through said return port; and means for associating each such image with customer information input into said customer input means.

3. A scrubs return cabinet according to claim 2, comprising a magnetic memory device for storing images from said camera and the associated customer information.

4. A scrubs return cabinet according to claim 1, wherein said return port includes a drawer above said landings zone of said one belt, which when pulled out from said housing to an open position is open at the top thereof to receive a returned garment, and when pushed in to a closed position permits the garment to drop to the landing zone therebelow.

5. A scrubs return cabinet according to claim 4, wherein said drawer has a divider therein so that a scrub top may be placed on one side of the divider and a scrub bottom may be placed on the other side of the divider.

6. A scrubs return cabinet according to claim 4 wherein said first and second belts are operative to compress said garments between them so as to increase the capacity of the return cabinet for said garments over a conventional return bin of the same size.

7. A scrubs return cabinet according to claim 1, wherein said return port is a top-loading door at a top end of said cabinet housing.

8. A scrubs return cabinet according to claim 1, comprising a discharge door located on a front of said cabinet housing, and which is adapted to be opened by laundry personnel to permit discharge of returned scrubs from said cabinet, and wherein said controller means and drive means are operative to turn said reels in a reverse direction so as to bring forward the scrubs that are compressed between said belts on said collecting reel, and discharge said scrubs through said discharge door.

9. A scrubs return cabinet according to claim 1, wherein said belts are formed of a synthetic resin material.

10. A scrubs return cabinet according to claim 9, wherein said synthetic resin material is selected from the group consisting of polypropylene, vinyl, and reinforced vinyl.

11. A scrubs return cabinet according to claim 9 wherein said synthetic resin material is TYVEK.

12. A scrubs return cabinet according to claim 1 wherein said belts are made of a mesh material.

* * * * *

UNITED STATES PATENT AND TRADEMARK OFFICE
CERTIFICATE OF CORRECTION

PATENT NO. : 6,439,500 B1  
DATED : August 27, 2002  
INVENTOR(S) : Norman A. Shoenfeld It is certified that error appears in the above-identified patent and that said Letters Patent is hereby corrected as shown below:

<u>Column 8,</u>  
Line 10, "landings" should read -- landing --.

Signed and Sealed this

Fourteenth Day of January, 2003

JAMES E. ROGAN  
*Director of the United States Patent and Trademark Office*